United States Patent
ElSohly et al.

(10) Patent No.: US 12,156,915 B2
(45) Date of Patent: Dec. 3, 2024

(54) SELECTED ARTEMISININ DIMERS FOR THE TREATMENT OF LASHMANIASIS

(71) Applicants: Mahmoud A. ElSohly, Oxford, MS (US); Waseem Gul, Oxford, MS (US)

(72) Inventors: Mahmoud A. ElSohly, Oxford, MS (US); Waseem Gul, Oxford, MS (US)

(*) Notice: Subject to any disclaimer, the term of this patent is extended or adjusted under 35 U.S.C. 154(b) by 531 days.

(21) Appl. No.: 17/433,594

(22) PCT Filed: Feb. 25, 2020

(86) PCT No.: PCT/US2020/019681
§ 371 (c)(1),
(2) Date: Aug. 24, 2021

(87) PCT Pub. No.: WO2020/176488
PCT Pub. Date: Sep. 3, 2020

(65) Prior Publication Data
US 2022/0175937 A1  Jun. 9, 2022

(51) Int. Cl.
*A61K 47/55* (2017.01)
*A61K 47/54* (2017.01)
*A61P 33/02* (2006.01)

(52) U.S. Cl.
CPC ............ *A61K 47/55* (2017.08); *A61K 47/542* (2017.08); *A61K 47/545* (2017.08); *A61P 33/02* (2018.01)

(58) Field of Classification Search
CPC .................................................... A61K 47/55
See application file for complete search history.

(56) References Cited

U.S. PATENT DOCUMENTS

| | | | |
|---|---|---|---|
| 6,790,863 B2 * | 9/2004 | ElSohly | C07D 519/00 549/348 |
| 7,098,242 B2 * | 8/2006 | ElSohly | A61P 33/02 549/348 |
| 7,842,720 B2 * | 11/2010 | Elsohly | A61P 31/00 549/348 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*

* cited by examiner

*Primary Examiner* — Nizal S Chandrakumar
(74) *Attorney, Agent, or Firm* — Hershkovitz & Associates, PLLC; Abe Hershkovitz; Eugene C. Rzucidlo

(57) ABSTRACT

New compositions are provided containing artemisinin dimers with high activity as anti-protozoal agents, including anti-malarial and anti-leishmanial properties, and methods for the treatment of protozoal infections, including malaria or leishmaniasis.

3 Claims, 5 Drawing Sheets

| Sample information | L. donovani Promastigotes IC50 µM | THP1 cells internalized L. donovani amastigotes IC50 µM | THP1 cytotoxicity IC50 µM | Selectivity index |
|---|---|---|---|---|
| Pentamidine | 1.907 ± 0.031 | 0.545 ± 0.019 | 31.284 ± 1.255 | 63 |
| Amphotericin B | 0.130± 0.012 | 0.062 ± 0.002 | 12.448 ± 0.296 | 201 |
| Dimer-O-sulphate | 0.0179± 0.0031 | 0.180 ± 0.005 | >14.188 ± NA | >79 |
| Dimer Piperdine | 0.217± 0.007 | 0.073 ± 0.034 | >14.453 ± NA | >198 |
| Dimer Piperzine | 0.173 ± 0.006 | 0.956 ± 0.433 | 14.433 ± NA | >15 |
| Dimer Morpholine | 0.0131± 0.004 | 0.007 ± 0.003 | >14.421 ± NA | >2052 |
| Dimer Valine | 0.032± 0.011 | 0.060 ± 0.009 | >13.814 ± NA | >230 |
| Dimer Dopamine | 1.119± 0.092 | 0.181 ± 0.157 | 13.159 ± NA | >73 |
| Dimer Tryptamine | 0.782± 0.033 | 0.045 ± 0.038 | 7.388 ± 2.490 | 165 |
| Dimer APD | 2.723± 0.161 | 0.511 ± 0.062 | >14.330 ± NA | >28 |
| Dimer Aniline | 1.429± 0.041 | 0.410 ± 0.005 | >14.288 ± NA | >35 |
| Dimer Serinol | 0.888± 0.025 | 0.164 ± 0.047 | >14.330 ± NA | >87 |
| Dimer-tboc-val | 4.733± 0.911 | 0.989 ± 0.246 | >12.136 ± NA | >12 |
| Dimer AB Acid | 0.0139± 0.0051 | 0.013 ± 0.003 | >13.194 ± NA | >999 |
| Dimer-GABA | 0.0133± 0.0041 | 0.013 ± 0.004 | >14.087 ± NA | >1086 |
| Dimer-Oxime | 5.645± 1.131 | 0.131 ± 0.014 | 11.383 ± 0.257 | 87 |
| Dimer-cyclohexylamine | 0.989± 0.004 | 0.158 ± 0.034 | >14.126 ± NA | >89 |
| Dimer-Oxime H.S. | 0.108± 0.011 | 0.062 ± 0.031 | >13.553 ± NA | >219 |
| Dimer benzylamine | 7.704± 1.773 | 0.099 ± 0.009 | >14.008 ± NA | >141 |
| Artemisinin | 99.175± 13.245 | >35.419 ± NA | >35.419 ± NA | 1 |

Figure 4/Table 1  Anti-leishmanial activity of artemisinin dimers in *Leishmania donovani* promastigotes and macrophage internalized amastigotes (parasite rescue and transformation assay), and cytotoxicity on differentiated THP1 cells. Values presented are mean ± S.D. of at least three observations.

| Sample information | THP1 cells - *L. donovani* Amastigotes digital image analysis (IC$_{50}$ µM) |
|---|---|
| Dimer AB Acid | 0.015 ± 0.004 |
| Dimer-GABA | 0.013 ± 0.005 |
| Dimer Morpholine | 0.009 ± 0.001 |
| Dimer-Oxime H.S. | 0.042 ± 0.003 |
| Dimer Tryptamine | 0.342 ± 0.020 |
| Dimer Valine | 0.350 ± 0.078 |
| Amphotericin B | 0.066 ± 0.002 |

Figure 5/Table 2  Anti-leishmanial activity of selected artemisinin dimers confirmed by the digital image analysis of macrophage amastigote assay. Values are mean ± S.D. of at least three observations.

SELECTED ARTEMISININ DIMERS FOR THE TREATMENT OF LASHMANIASIS

FIELD OF THE INVENTION

The present invention relates to improving the therapeutic utility of "artemisinin-based dimers" in the treatment of protozoal infections including, e.g., visceral Leishmaniasis.

BACKGROUND OF THE INVENTION

Leishmaniasis is a neglected tropical disease which mainly affects the poor population in developing countries. More than 350 million people are considered at the risk of contracting leishmaniasis, and around 2 million new cases occur every year (1). Leishmania exists in three major clinical forms: cutaneous, mucocutaneous and visceral leishmaniasis (2). Visceral leishmaniasis (VL) is caused by the Leishmania donovani parasite, and is fatal if left untreated (2). The choice of drugs available to treat visceral leishmaniasis is already very limited, and even those drugs suffer from poor efficacy and high toxicities at therapeutic doses (3).

Most of the first line anti-leishmanial drugs have already lost their utility due to increasing multiple drug resistance (4). The current discovery pipeline of anti-leishmanial drugs is also severely depleted. Sustained efforts are needed to enrich new anti-leishmanial drug discovery pipelines.

Artemisinins are sesquiterpene lactones which have been primarily exploited as anti-malarial agents. Artemisinins have a unique chemical structure with an endoperoxide ring, which is different from the other standard quinolone-type of anti-malarials, which help in significantly more rapid clearance of malaria parasites from the blood than other available anti-malarials (6). Artemisinins are universally converted to its active metabolite, dihydroartemisinin (DHA) in the body (7, 8). Artemisinins have several advantages, including fast action, with low propensity to develop resistance and selective mechanisms of action (9, 10). They have excellent safety profiles, negligible toxicities, and an outstanding therapeutic window.

Several derivatives of artemisinins have been developed with higher efficacy for anti-malarial treatment and with a better chemical profile to overcome the issues related to bioavailability and stability under physiological environments (11, 12). Artemisinin derivatives have also been investigated for their potential application in treatment of several non-antimalarial conditions, including cancers, inflammatory diseases, viral diseases, leishmaniasis and other infectious diseases (13, 14).

Artemisinin and its derivatives have been reported for the first time for anti-leishmanial activity against Leishmania major, the causative agent for cutaneous leishmaniasis (15). Subsequently, several other groups reported the anti-leishmanial activity of artemisinins in Leishmania major (16, 17). Studies related to activity of artemisinin against L. donovani are very limited (18-20). Artemisinin has been reported for it anti-leishmanial activity against L. donovani promastigotes at very high concentrations (21), and its activity is notably absent against amastigotes which are the biologically relevant form of the parasite. Artemisinin also has been reported for anti-leishmanial activity in BALB/c mice that were infected with L. donovani (17).

The object of the present invention is to develop artemisinin dimers which are safe, and with a short treatment course (<10 days) as anti-leishmanial drugs (for increased compliance), and to increase the clinical efficacy of artemisinin dimers.

SUMMARY OF THE INVENTION

This invention comprises compositions containing artemisinin dimers with activity as anti-protozoal agents, including anti-malarial and anti-leishmanial properties. This invention also describes methods for the treatment of protozoal infections, including malaria or leishmaniasis. The compositions of this invention have not been previously described.

Most of the monomers of artemisinin and its derivatives suffer from the lack of oral bioavailability (22, 23). The present artemisinin dimers were designed to improve these formulation characteristics.

In parallel, the present dimers were screened against the different forms of L. donovani parasite. The present artemisinin dimers were found to have potent anti-leishmanial activity.

Furthermore, the present artemisinin dimers were evaluated for the molecular mode of their anti-leishmanial action. Artemisinin and its derivatives are reported for its apoptotic effect on the L. donovani promastigote parasite (20, 24). In this regard, the presently most potent artemisinin dimers, dimer Morpholine, and dimer gamma-aminobutyric acid (GABA), were selected for evaluating the apoptotic response on the promastigote form of the parasite with the help of annexin V binding assay.

Both dimer Morpholine and dimer GABA show time-dependent apoptotic effect. The parent compound, artemisinin, does not have an anti-leishmanial effect, and apoptotic effect at 35 µM concentration. The present artemisinin dimers can be optimized for oral bio-availability and other pharmacokinetic/pharmacodynamic (PK/PD) characteristics for leishmania treatments. Furthermore, the present artemisinin dimers have a low cost of production which is an important requirement for treatment of visceral leishmaniasis in the poor population in a developing country.

BRIEF DESCRIPTION OF THE FIGURES

FIG. 4/Table 1 is a digital image analysis assay; and

FIG. 5/Table 2 is anti-leishmanial activity of selected Artemisinin dimers.

DETAILED DESCRIPTION OF THE INVENTION

Figure 1:
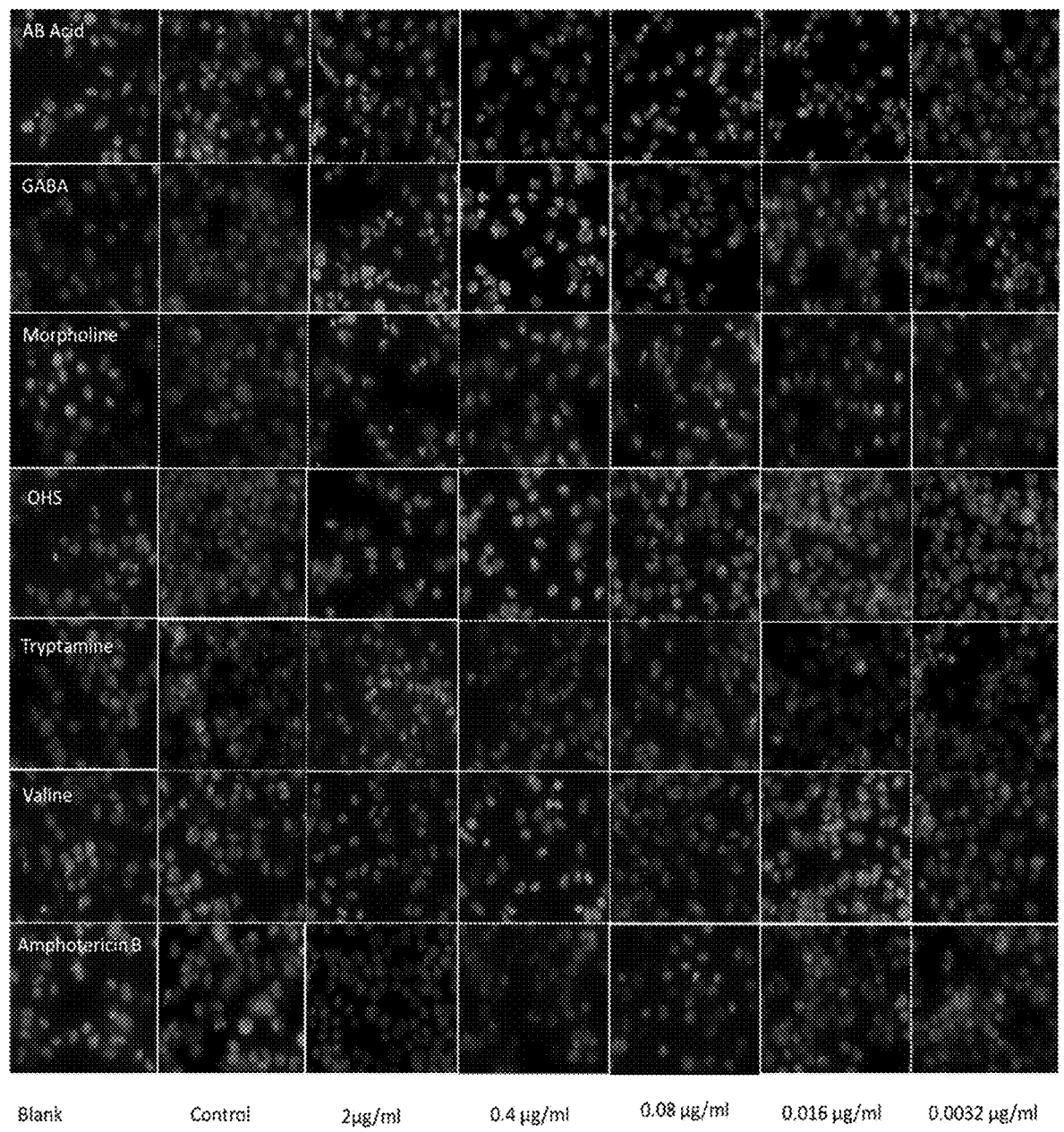
FIG. 1 shows macrophage amastigote assays for artemisinin dimers by digital image analysis by nucleic acid staining using Leishmania donovani amastigotes as parasites and differentiated THP1 cells as host cells.

With the goal of improving therapeutic utility of the artemisinins, several "artemisinin-based dimers" were synthesized by the inventors. Synthesized compounds were a series of artemisinin dimers that include Dimer with O-sulphate, Piperdine, Piperazine, Morpholine, Valine, Dopamine, Tryptamine, 3-amino-1,2-propanediol (APD), Aniline, Serinol, boc-valine, 4-aminomethyl-benzoic acid (AB acid), gamma aminobutyric acid (GABA), Oxime, cyclohexylamine, Oxime Hemisuccinate and Benzylamine.

A schematic representation of the synthetic protocol for artemisinin dimers is as follows:
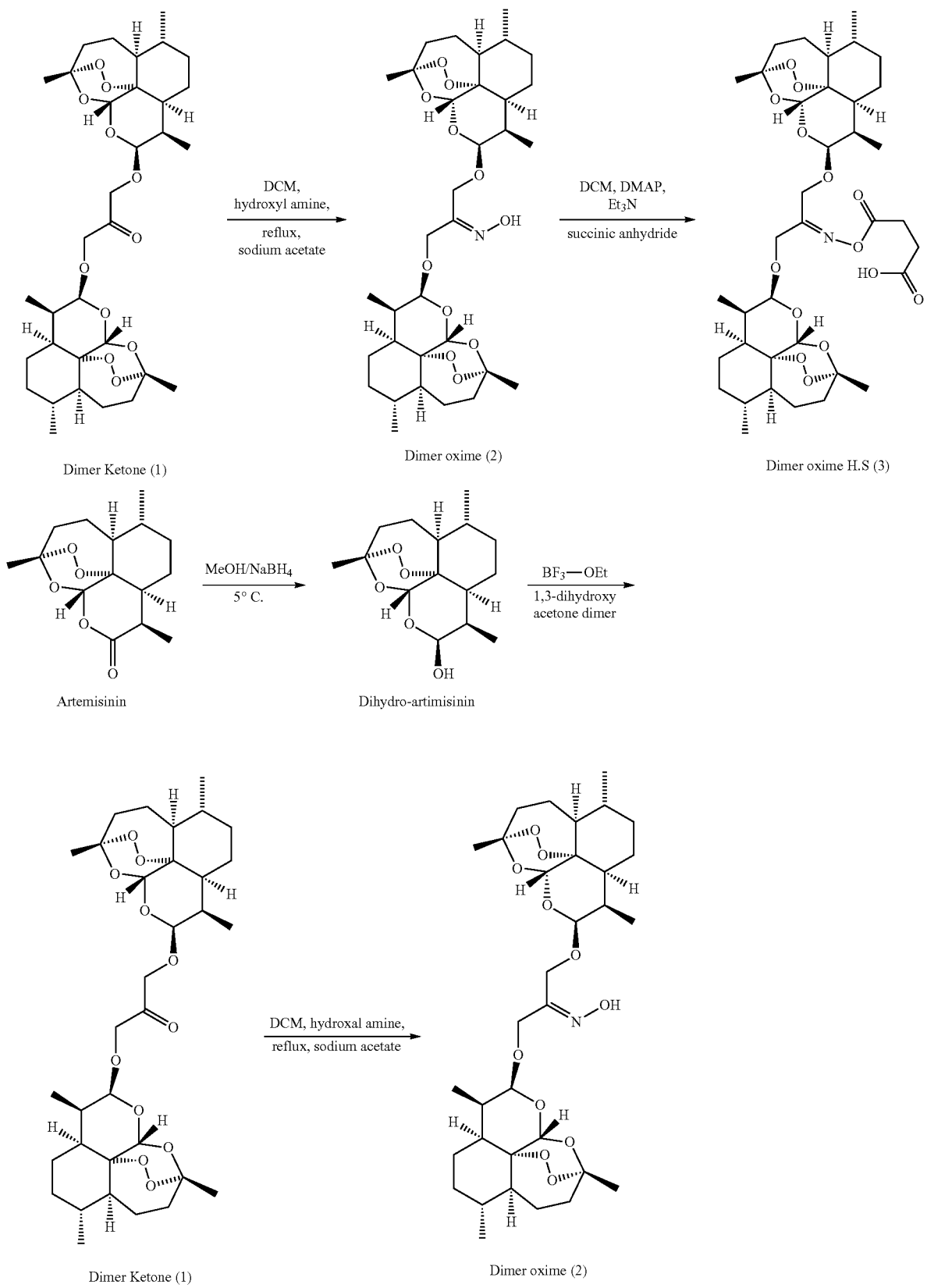

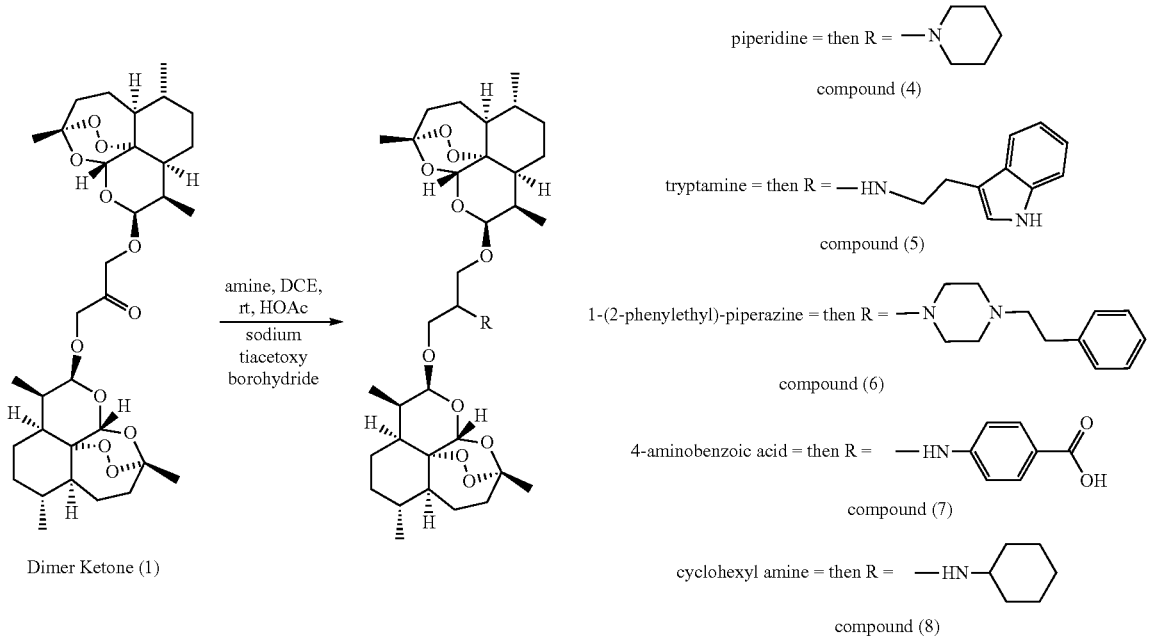
The structures of artemisinin dimers tested for anti-leishmanial activities include:
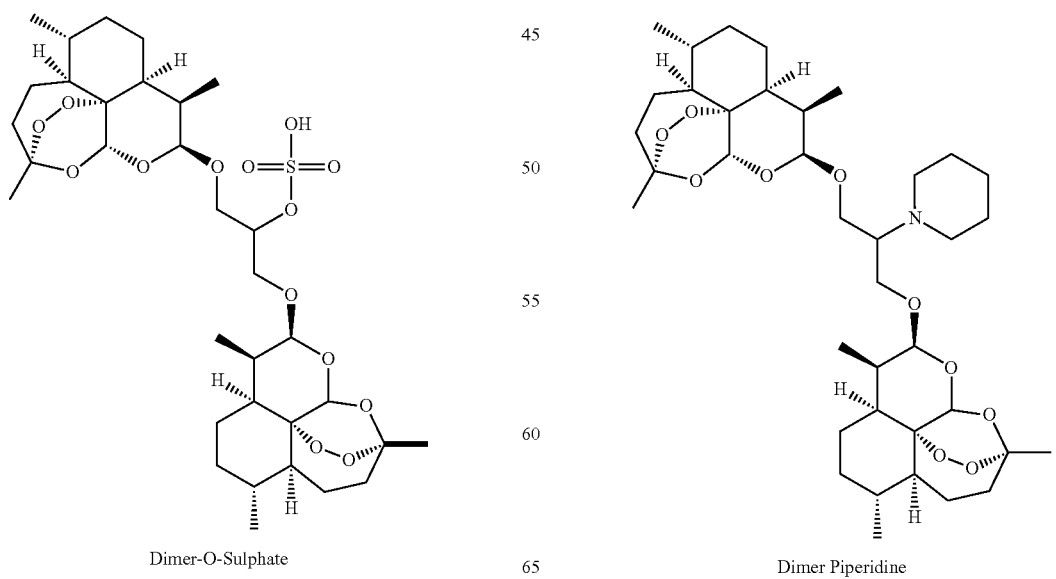

-continued
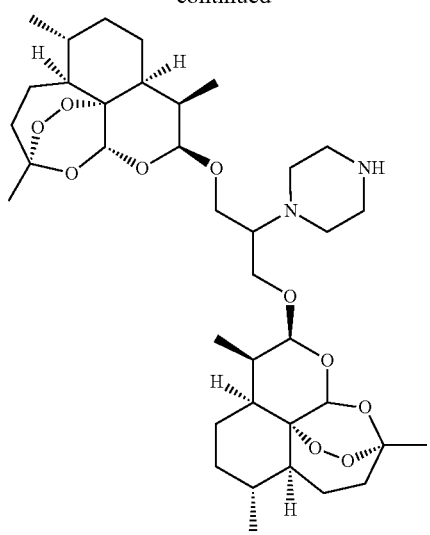
Dimer Piperazine
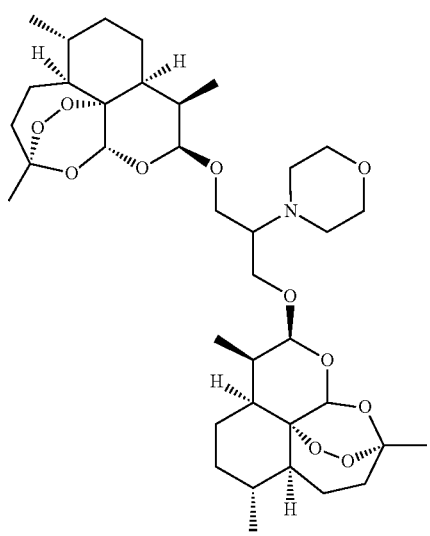
Dimer Morpholine
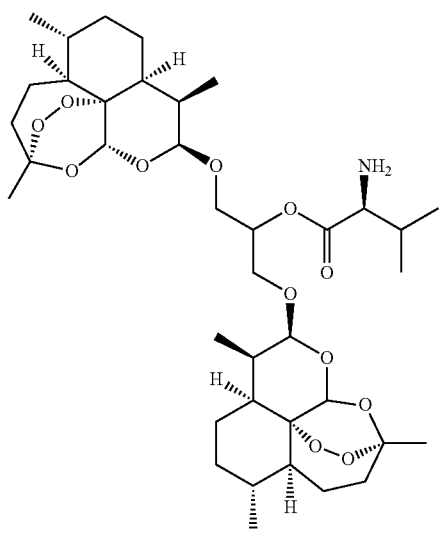
Dimer Valine
-continued
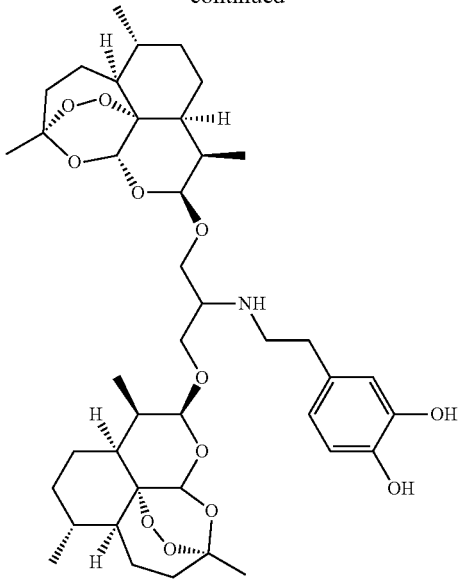
Dimer Dopamine
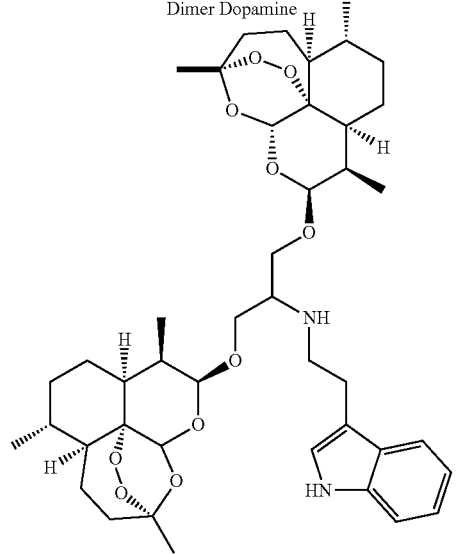
Dimer Tryptamine
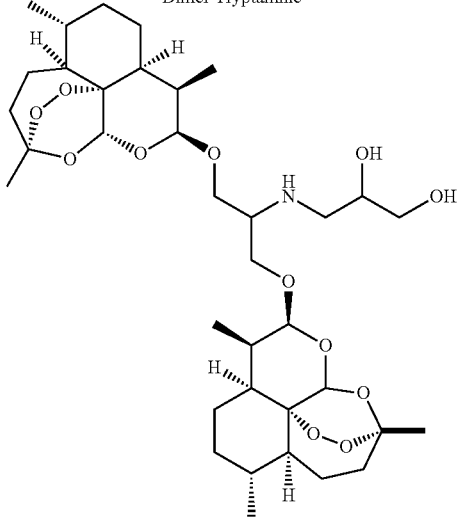
Dimer 3-amino-1,2-propanediol

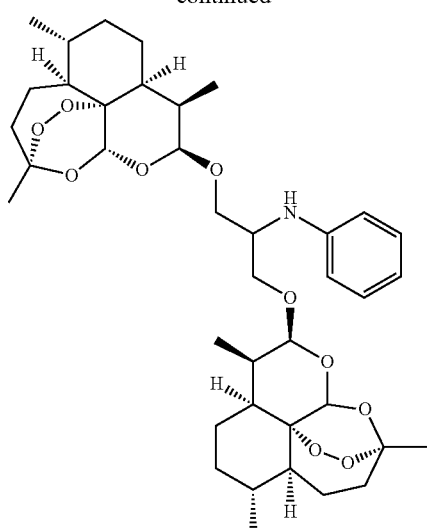
Dimer Aniline
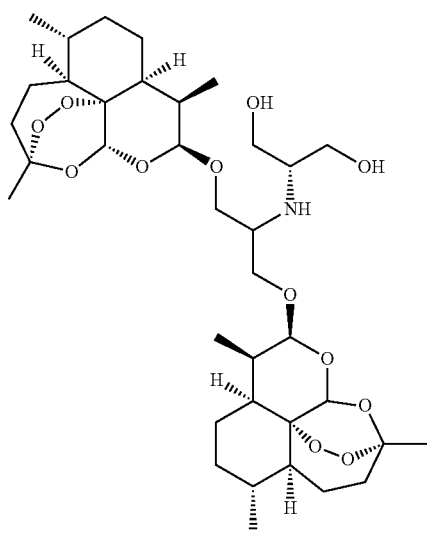
Dimer Serinol
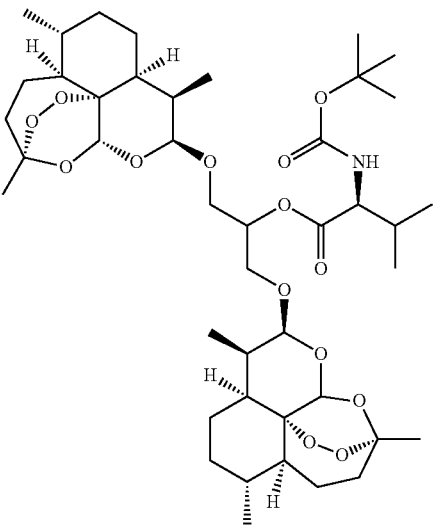
Dimer-tboc-val
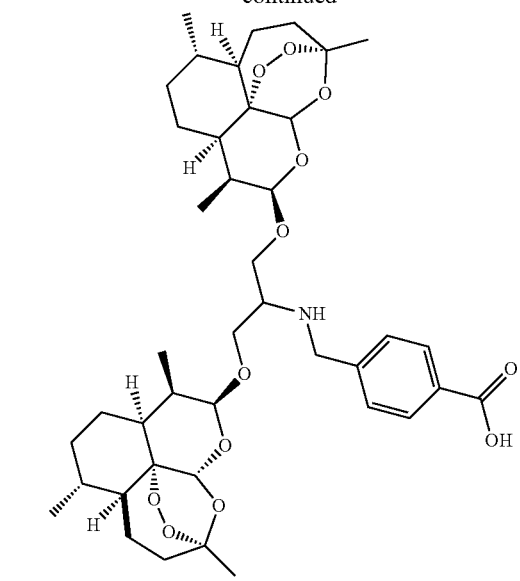
Dimer AB acid
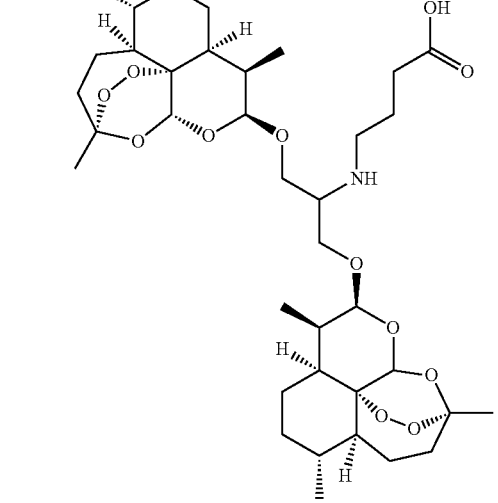
Dimer-GABA
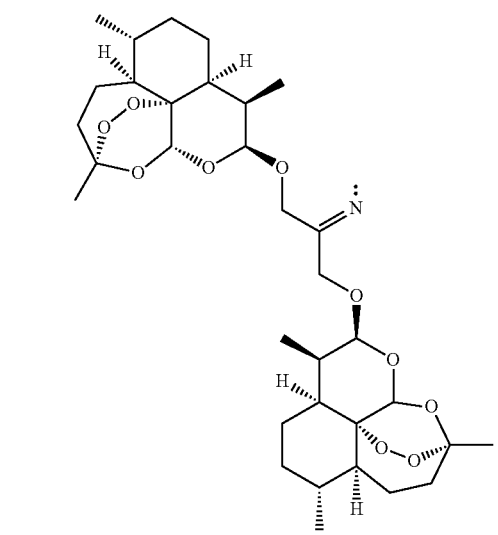
Dimer Oxime

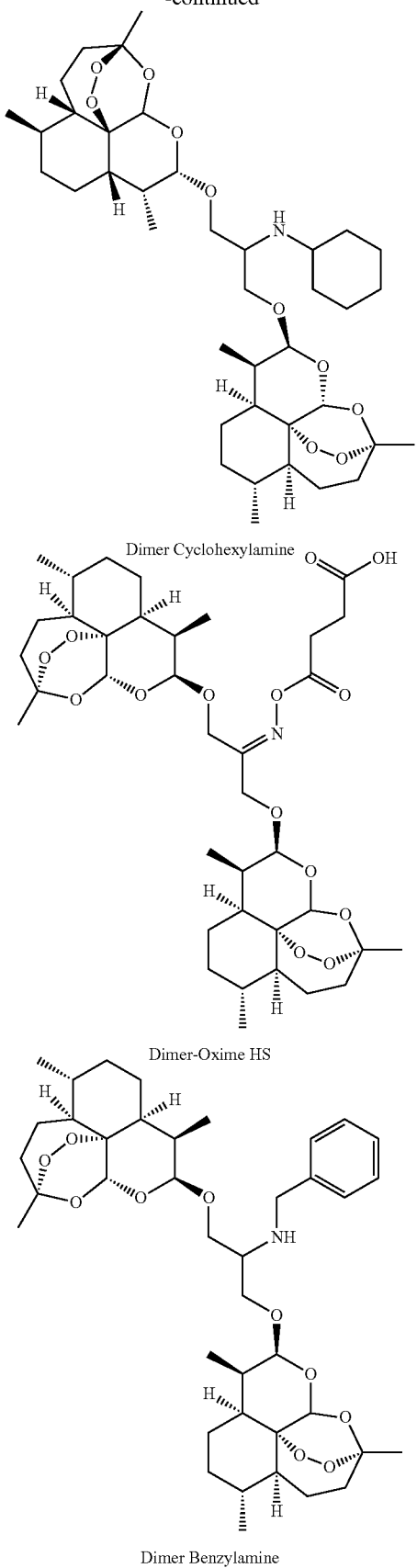

Dimer Cyclohexylamine

Dimer-Oxime HS

Dimer Benzylamine

DETAILED DISCUSSION OF PREFERRED EMBODIMENTS

Administration of the instant dimers may be by any of the conventional routes of administration, for example, oral, subcutaneous, intraperitoneal, intramuscular, intravenous or rectally. In a preferred embodiment, the compound is administered in combination with a pharmaceutically-acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include saline, water, buffer solutions, and edible oils, e.g., peanut and corn oils.

When administered in solid form, the compound and diluent carrier may be in the form of tablets, capsules, powders, or suppositories, prepared by any of the well-known methods. When given as a liquid preparation, the mixture of active compound and liquid diluent carrier may be in the form of a suspension administered as such, an emulsion, or a true solution. The compound is administered in a non-toxic dosage concentration sufficient to inhibit the growth and/or destroy cancer, or prevent cancer metastasis, or to destroy protozoal organisms such as malaria and leishmania. The actual dosage unit will be determined by well-recognized factors such as body weight of the patient and/or severity and type of pathological condition the patient might be suffering.

With these considerations in mind, the dosage unit for a particular patient can be readily determined by the medical practitioner in accordance with the techniques known in the medical arts.

The present invention brings new possibilities to the field of anti-leishmaniasis drug discovery, demonstrating that artemisinin dimers may evolve as anti-leishmanial agents with better efficacy and without toxicity. The present invention is quite relevant as leishmaniasis is a neglected tropical disease, and visceral leishmaniasis is the second most prolific killer in tropical diseases after malaria (1).

There are several factors responsible for the deaths due to visceral leishmaniasis. First, most of the affected population is poor, with the low living standards. Currently, the affected population is unable to afford a food supply, and most of the treatments are very costly (25, 26). Also, most of the available treatments have severe toxicities (27).

Some of the first line drugs like amphotericin B is formulated to liposomal form (Amphisome), but the cost of formulation again increases the cost (28). Sodium stibogluconate was the only primary anti-leishmanial drug, but most of the epidemic areas become fully resistant to this drug (4). There are several other cases also reported for resistance. Recently introduced is the only oral drug, miltefosine (29, 30). Pentamidine and sitamaquine are already out of the market due to low efficacy for visceral leishmaniasis (31).

It is very necessary to develop better medication with high efficacy, a better safety profile and lower cost that is less susceptible to resistance development. Artemisinin is a natural product isolated from *Artemisia annua*, and offers a better, cheaper alternative here, but artemisinin is not reported with potent anti-leishmanial activity (5).

The present artemisinin dimers have potent anti-leishmanial activity for both the promastigote and intracellular amastigote form of the *L. donovani* parasite. Most of the artemisinin dimers do not show toxicity on differentiated THP1 cells (human acute leukemia cells). The artemisinin dimers have much better selectivity profiles than control anti-leishmanial drugs amphotericin (IC50 0.062 µM, SI 201) and pentamidine (IC50 0.545 µM, SI 63).

Several other artemisinin derivatives have been investigated. Most of them have activity either higher or equivalent to control drugs (Sitamaquine, miltefosine, amphotericin B or Pentamidine) (14, 19, 32).

In the present invention, artemisinin dimers are reported with higher activity and higher selectivity than the control drugs amphotericin B and pentamidine. Dimer Morpholine and Dimer GABA have SI >2056 and >1086, respectively. Here, for the first time, some anti-leishmanial drug leads (Dimer Morpholine and Dimer GABA) are reported with such high selectivity profiles.

Figure 2:
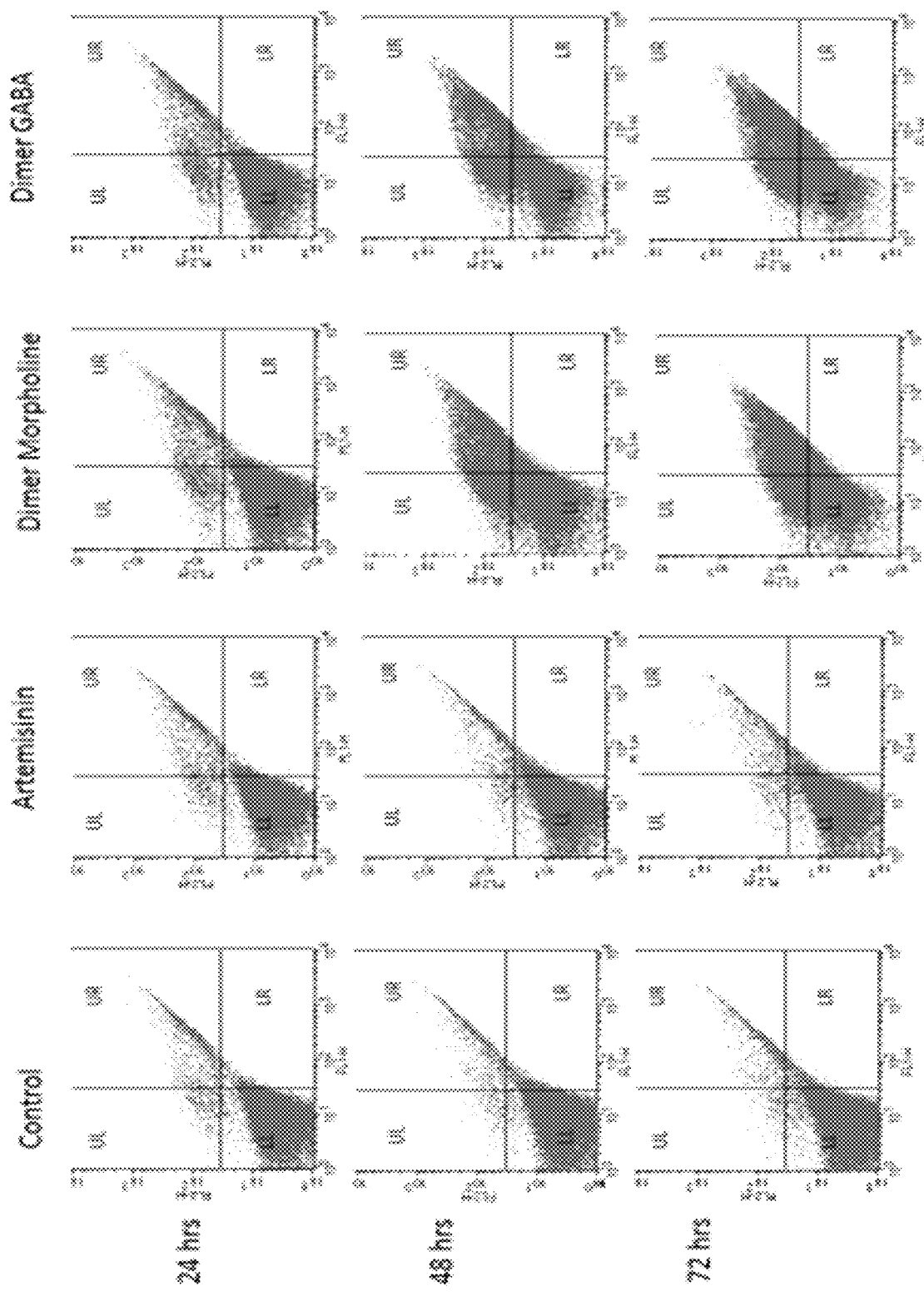
FIG. 2 is a panel of FL2/FL1 dot plots with different time intervals of treatment with parent artemisinin, Dimer Morpholine, and Dimer GABA.

These two molecules were further evaluated for their mode of leishmanicidal action. Both dimers show apoptotic effect on the promastigote form of the parasite and this apoptotic effect gradually increases from 24 hrs. to 72 hrs. (FIG. 2). The parent artemisinin does not have leishmanicidal or apoptotic effect. A separate study (unpublished) shows that the artemisinin dimers have significantly higher bioavailability than the parent drug artemisinin. The present dimers could be developed as oral formulations, and have potential for oral treatment of visceral leishmaniasis. These preliminary data will be further helpful in the evaluation of the molecular mechanism of action of these novel drug leads. Furthermore, artemisinin dimers already have several factors like low cost of synthesis, better bioavailability profile, better selectivity profile and less susceptibility to resistance. Thus, these novel artemisinin dimers could be developed as better anti-leishmanial drugs for visceral leishmaniasis.

RESULTS

Cytotoxicity and Anti-Leishmanial Activity

Figure 3:
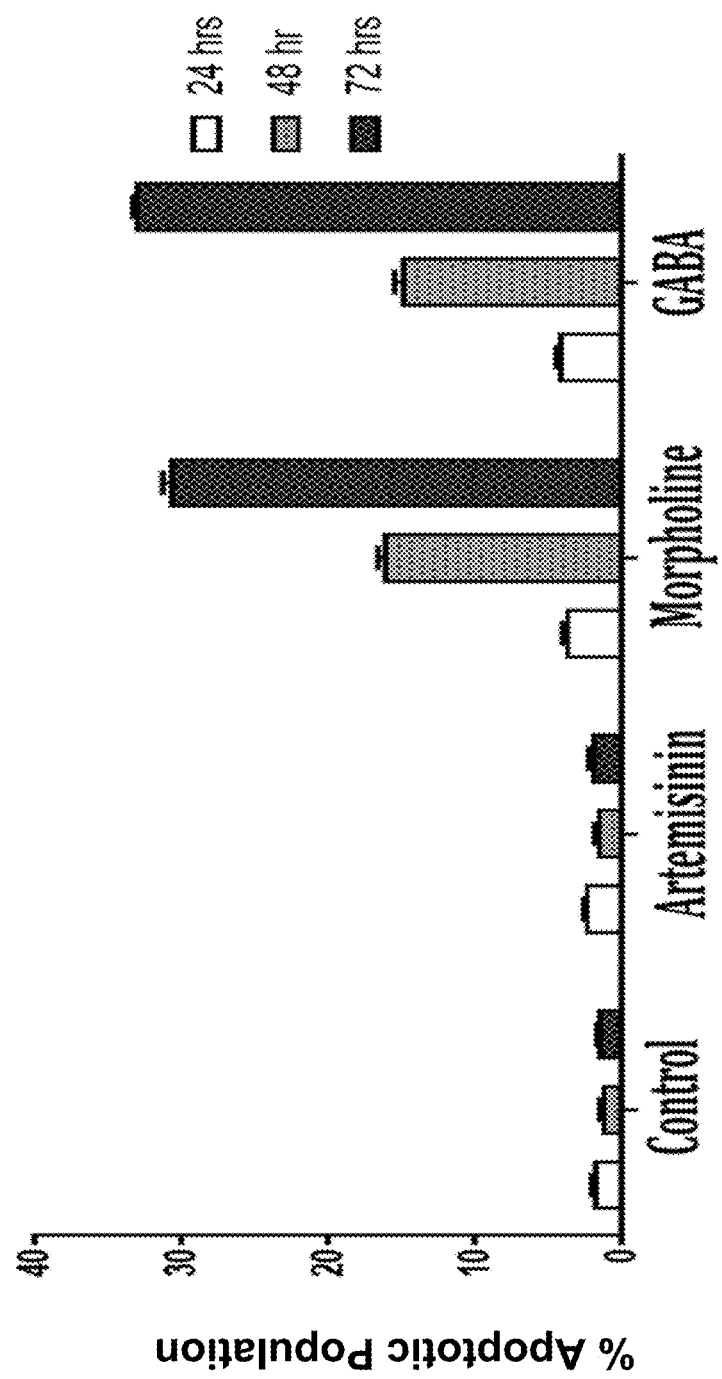
FIG. 3 is a chart of the apoptotic effect of Dimer Morpholine and Dimer GABA in comparison to untreated and parent artemisinin treated promastigotes at different time intervals.

Cytotoxicity was evaluated on differentiated THP1 cells. None of the compounds was toxic to differentiated THP1 cells except dimer tryptamine (IC50 7.388 µM) and dimer oxime (IC50 11.383 µM). Anti-leishmanial activity of all artemisinin dimers, parent artemisinin, and control drugs amphotericin B and pentamidine, were evaluated on the promastigote and intracellular amastigote forms of $L.$ $donovani$ parasite (Table 1). All artemisinin dimers show potent activity on the promastigote form of the parasite by alamar blue assay. All artemisinin dimers show potent activity on the intracellular amastigote form of the parasite in parasite rescue and transformation assay (Table 1). Parent artemisinin shows activity on the promastigote form of the parasite at very high concentration (IC50 99.175 µM), and does not have any activity till 35.419 µM concentration in intracellular amastigotes (concentrations are limited in parasite rescue and transformation assay due to the fact that the permissible limit of DMSO on THP1 cells was 0.5%). A selectivity index (SI) for each artemisinin dimer was calculated by dividing the IC50 value of cytotoxicity by the IC50 value of anti-leishmanial activity in the parasite rescue and transformation assay. Dimer Morpholine (0.007 µM, SI >2052) and Dimer GABA (0.013 µM, SI >1086) were the most active artemisinin dimers with the highest selectivity indices. Digital image analysis assay reconfirmed the anti-leishmanial activity of selected artemisinin dimers that showed potent activity previously in parasite rescue and transformation assay (Table 2). Infectivity in differentiated THP1 cells was calculated by dividing the number of amastigote nuclei by the number of THP1 cell nuclei. Selected artemisinin dimers show potent activity against the intracellular amastigotes in digital image analysis assay too (FIG. 3/Table 2).

Apoptosis Study

Two-Way ANOVA with Tukey Comparison Test (FIG. 2):

In 24 hrs., Dimer Morpholine 14 µM has a significantly (P<0.0001) higher population in an Upper Right (UR, Late apoptosis) area in a FL2 (PI)/FL1 (Annexin FITC) dot plot compared to the control group. Dimer GABA 14 µM has a significantly (P<0.0001) higher population in an UR area in a FL2/FL1 dot plot compared to the control group. In 48 hrs., Dimer Morpholine 14 µM has a significantly (P<0.0001) higher population in an UR area in a FL2/FL1 dot plot compared to the control group. Dimer GABA 14 µM has a significantly (P<0.0001) higher population in an UR area in a FL2/FL1 dot plot compared to the control group. In 72 hrs., Dimer Morpholine 14 µM has a significantly (P<0.0001) higher population in an UR area in a FL2/FL1 dot plot compared to the control group. Dimer GABA 14 µM (P<0.0001) has a significantly higher population in an UR area in a FL2/FL1 dot plot compared to the control group. Dimer Morpholine 14 µM in 48 hrs. has a significantly (P<0.0001) higher population in an UR area in a FL2/FL1 dot plot compared to Dimer Morpholine 14 µM in 24 hrs. Dimer GABA 14 µM in 48 hrs. has a significantly (P<0.0001) higher population in an UR area in a FL2/FL1 dot plot compared to Dimer GABA 14 µM in 24 hrs. Dimer Morpholine 14 µM in 72 hrs. has a significantly (P<0.0001) higher population in an UR area in a FL2/FL1 dot plot compared to Dimer Morpholine 14 µM in 24 hrs. Dimer GABA 14 µM in 72 hrs. has a significantly (P<0.0001) higher population in an UR area in a FL2/FL1 dot plot compared to Dimer GABA 14 µM in 24 hrs.

Cell Lines

THP-1 cells (human monocytic leukemia cells) were made available by the American Type Culture Collection (ATCC) and were maintained in RPMI 1640 media (Life-Technologies) supplemented with Sodium Pyruvate, Glutamine, HEPES (Life-81 Technologies) and 10% heat-inactivated FBS (Sigma). The culture was maintained at 37° C. in 5% $CO_2$ incubator. THP1 cells Subculture was done every 3-4 days. Promastigote forms of $Leishmania$ $donovani$ (S1 strain) was grown in RPMI 1640 medium at pH 7.4 supplemented with 10% fetal bovine serum. The culture was maintained at 26° C. by incubator. Subculture was done every 3-4 days.

$Leishmania$ $donovani$ Promastigote Assay

The promastigote assay was based on alamar blue base growth analysis (33). A 3-4 day old promastigote culture in the exponential phase was diluted with RPMI 1640 medium, to $1 \times 10^6$ cells/ml. Artemisinin dimer samples were diluted to stock concentration of 2 mg/ml. Artemisinin dimer samples were dispensed in culture plates and diluted with a promastigote culture so the final highest concentration of samples was 10 µg/ml, and highest concentration of parent artemisinin was 40 µg/ml. The culture with the highest concentration of each artemisinin dimer was serially diluted in 1:5 ratio to 6 different concentrations. All artemisinin dimers were tested in triplicate. Culture plates with the promastigote parasites and artemisinin dimers were incubated at 26° C. for 48 hrs. After 48 hrs., alamar blue was added to each well and the plates were incubated further for 24 hrs. Standard fluorescence was measured on a Fluostar Galaxy fluorometer (BMG LabTechnologies) at 544 nm ex, 590 nm em. The dose response curves were prepared using XLfit 5.2.2 software (34).

Macrophages Internalized *L. donovani* Amastigote Assays Parasite Rescue and Transformation Assay:

This assay is based on the previously published protocol by Jain et al. (35). A 3-day old culture of THP1 cells in the exponential phase was diluted with RPMI medium to $2.5 \times 10^5$ cells/ml. PMA was added to final a concentration of 25 ng/ml. PMA treated culture was dispensed in clear flat bottom culture plates and incubated overnight at 37° C. in a 5% $CO_2$ incubator. The plates with differentiated THP1 Cells were washed with serum-free medium with the help of Molecular device AquaMax 4000. A 5-6-day old *L. donovani* promastigote culture diluted to $5 \times 10^6$ cells/ml was added over differentiated THP1 cells. The Macrophage cells to parasite ratio for infection was 1:10. The plates were incubated for 24 hrs. After 24 hrs., the plates were again washed with the help of AquaMax 4000 and the serum-free medium was replaced by a medium with diluted test samples. The plates were placed again in a $CO_2$ incubator at 370° C. for 48 hrs. After 48 hrs., the macrophage amastigote plates were washed and treated with 0.05% SDS for 30 secs., and diluted SDS medium was immediately replaced with complete RPMI medium. Plates were incubated for amastigote to promastigote transformation, and promastigote growth at 260° C. for 48 hrs. After 48 hrs., 5 μl of alamar blue was added to each well of macrophage amastigote assay plates, and the plates were incubated further for 24 hrs. Standard fluorescence was measured on a Fluostar Galaxy fluorometer (BMG LabTechnologies) at 544 nm ex, 590 nm em. Xlfit 5.3.1 software has generated all dose response curves.

Digital Image Analysis Assay

A 3-day old culture of THP1 cells in the exponential phase was diluted with RPMI medium to $2.5 \times 10^5$ cells/ml. PMA was added to final a concentration of 25 ng/ml. PMA treated culture was dispensed in the 16 well chamber slides and incubated overnight at 37° C. in a 5% $CO_2$ incubator. The 16 well chamber slides with differentiated THP1 cells were washed with serum-free medium. A 5-6-day old *L. donovani* promastigote culture diluted to $5 \times 10^6$ cells/ml was added over differentiated THP1 cells. The Macrophage cells to parasite ratio for infection was 1:10. The 16 well chamber slides were incubated for 24 hrs. After 24 hrs., chamber slides were again washed, with the remaining serum-free medium replaced with complete medium with diluted test samples. The chamber slides were placed again in a $CO_2$ incubator at 370° C. for 48 hrs. After 48 hrs., the macrophage amastigote plates were washed and fixed with 100% methanol for 30 secs. The fixed chamber slides were stained with 5× CybrGreen I for 15 mins. All the images of differentiated THP1 cells infected with *L. donovani* amastigote parasites were collected by a NIKON 90i Eclipse fluorescent microscope. The differential counting of a number of THP1 cells and number of amastigotes in THP1 cells was done by ImageJ software (35).

THP1 Cytotoxicity Assay

A 3-day old culture of THP1 cells in the exponential phase was diluted with RPMI medium to $2.5 \times 10^5$ cells/ml. PMA was added to final a concentration of 25 ng/ml. PMA treated culture was dispensed in clear flat bottom culture plates and incubated overnight at 37° C. in a 5% $CO_2$ incubator. The plates with differentiated THP1 cells were washed with serum-free medium with the help of Molecular device AquaMax 4000 and the serum-free medium was replaced by a medium with diluted test samples. The plates were placed again in a $CO_2$ incubator at 370° C. for 48 hrs. After 48 hrs., 2.5 ul of alamar-blue was added to each well of cytotoxicity plates, and the plates were incubated further for 24 hrs.

Standard fluorescence was measured on a Fluostar Galaxy fluorometer (BMG LabTechnologies) at 544 nm ex, 590 nm em. All dose response curves have been generated by Xlfit 5.3.1 software (36).

Annexin V Binding Apoptosis Assay

Apoptosis, also known as programmed cell death, is a physiological process of removal of unwanted cells (37). In one of the earlier events, the process of apoptosis includes translocation of membrane phosphatidylserine from the inner side of the cell membrane to the surface (38). Annexin V is a $Ca^{++}$ dependent phospholipid-binding protein which has a high affinity for phosphatidylserine (39). So FITC-labeled Annexin V can be used for the analysis of exposed PS using a flow cytometer (40). Apoptosis analysis was done by flow cytometry using Annexin V/Propidium Iodide staining method. Most active with a high selectivity index, artemisinin dimers were selected for apoptosis study (41). $1 \times 10^7$ promastigote cells/ml were treated with artemisinin (35 μM), dimer Morpholine (14 μM) and dimer GABA (14 μM). Aliquots were withdrawn at different time intervals and stained with FITC-Annexin V and Propidium Iodide. The cell was analyzed by flow-cytometry. As shown in FIG. 2, the gated population was selected in a FFC/SSC dot plot for healthy promastigote cells. 50,000 in a gated event were run in a FL2 (Propidium Iodide)/FL1 (Annexin FITC) and analyzed by quadrangle plot.

REFERENCES

1. WHO Expert Committee on the Control of the Leishmaniases. Meeting (2010: Geneva), World Health Organization. 2010. Control of the leishmaniases: report of a meeting of the WHO Expert Committee on the Control of Leishmaniases, Geneva, 22-26 Mar. 2010. World Health Organization, Geneva.
2. Herwaldt B L. 1999. Leishmaniasis. Lancet 354:1191-1199.
3. Croft S L, Seifert K, Yardley V. 2006. Current scenario of drug development for leishmaniasis. Indian J Med Res 123:399-410.
4. Croft S L, Sundar S, Fairlamb A H. 2006. Drug resistance in leishmaniasis. Clin Microbiol Rev 19:111-126.
5. van Agtmael M A, Eggelte T A, van Boxtel C J. 1999. Artemisinin drugs in the treatment of malaria: from medicinal herb to registered medication. Trends Pharmacol Sci 20:199-205.
6. Kremsner P G, Krishna S. 2004. Antimalarial combinations. Lancet 364:285-294.
7. Zhu D Y, Huang B S, Chen Z L, Yin M L, Yang Y M, Dai M L, Wang B D, Huang Z H. 1983. [Isolation and identification of the metabolite of artemisinine in human]. Zhongguo Yao Li Xue Bao 4:194-197.
8. Mi J F. 1991. [Studies on circular dichroism of some reactional intermediates of artemisinine and artemisinine in B]. Yao Xue Xue Bao 26:557-560.
9. Haynes R K, Krishna S. 2004. Artemisinins: activities and actions. Microbes Infect 6:1339-1346.
10. Krishna S, Uhlemann A C, Haynes R K. 2004. Artemisinins: mechanisms of action and potential for resistance. Drug Resist Updat 7:233-244.

11. Guo J, Guiguemde A W, Bentura-Marciano A, Clark J, Haynes R K, Chan W C, Wong H N, Hunt N H, Guy R K, Golenser J. 2012. Synthesis of artemiside and its effects in combination with conventional drugs against severe murine malaria. Antimicrob Agents Chemother 56:163-173.
12. Singh C, Kanchan R, Chaudhary S, Puri S K. 2012. Linker-based hemisuccinate derivatives of artemisinin: synthesis and antimalarial assessment against multidrug-resistant *Plasmodium yoelii nigeriensis* in mice. J Med Chem 55:1117-1126.
13. Ho W E, Peh H Y, Chan T K, Wong W S. 2014. Artemisinins: pharmacological actions beyond anti-malarial. Pharmacol Ther 142:126-139.
14. Loo C S, Lam N S, Yu D, Su X Z, Lu F. 2017. Artemisinin and its derivatives in treating protozoan infections beyond malaria. Pharmacol Res 117:192-217.
15. Yang D M, Liew F Y. 1993. Effects of qinghaosu (artemisinin) and its derivatives on experimental cutaneous leishmaniasis. Parasitology 106 (Pt 1):7-11.
16. Esavand Heydari F, Ghaffarifar F, Soflaei S, Dalimi A. 2013. Comparison Between in Vitro Effects of Aqueous Extract of *Artemisia seiberi* and Artemisinin on *Leishmania major*. Jundishapur J Nat Pharm Prod 8:70-75.
17. Ghaffarifar F, Esavand Heydari F, Dalimi A, Hassan Z M, Delavari M, Mikaeiloo H. 2015. Evaluation of Apoptotic and Antileishmanial Activities of Artemisinin on Promastigotes and BALB/C Mice Infected with *Leishmania major*. Iran J Parasitol 10:258-267.
18. Sen R, Ganguly S, Saha P, Chatterjee M. 2010. Efficacy of artemisinin in experimental visceral leishmaniasis. Int J Antimicrob Agents 36:43-49.
19. Chollet C, Crousse B, Bories C, Bonnet-Delpon D, Loiseau P M. 2008. In vitro antileishmanial activity of fluoro-artemisinin derivatives against *Leishmania donovani*. Biomed Pharmacother 62:462-465.
20. Islamuddin M, Farooque A, Dwarakanath B S, Sahal D, Afrin F. 2012. Extracts of *Artemisia annua* leaves and seeds mediate programmed cell death in *Leishmania donovani*. J Med Microbiol 61:1709-1718.
21. Avery M A, Muraleedharan K M, Desai P V, Bandyopadhyaya A K, Furtado M M, Tekwani B L. 2003. Structure-activity relationships of the antimalarial agent artemisinin. 8. design, synthesis, and CoMFA studies toward the development of artemisinin-based drugs against leishmaniasis and malaria. J Med Chem 46:4244-4258.
22. Titulaer H A, Zuidema J, Kager P A, Wetsteyn J C, Lugt C B, Merkus F W. 1990. The pharmacokinetics of artemisinin after oral, intramuscular and rectal administration to volunteers. J Pharm Pharmacol 42:810-813.
23. Medhi B, Patyar S, Rao R S, Byrav D S P, Prakash A. 2009. Pharmacokinetic and toxicological profile of artemisinin compounds: an update. Pharmacology 84:323-332.
24. Sen R, Saha P, Sarkar A, Ganguly S, Chatterjee M. 2010. Iron enhances generation of free radicals by Artemisinin causing a caspase-independent, apoptotic death in *Leishmania donovani* promastigotes. Free Radic Res 44:1289-1295.
25. Gurunath U, Joshi R, Agrawal A, Shah V. 2014. An overview of visceral leishmaniasis elimination program in India: a picture imperfect. Expert Rev Anti Infect Ther 12:929-935.
26. Sunyoto T, Potet J, Boelaert M. 2017. Visceral leishmaniasis in Somalia: A review of epidemiology and access to care. PLoS Negl Trop Dis 11:e0005231.
27. Jha R K, Sah A K, Shah D K, Sah P. 2013. The treatment of visceral leishmaniasis: safety and efficacy. JNMA J Nepal Med Assoc 52:645-651.
28. Jain K, Jain N K. 2013. Novel therapeutic strategies for treatment of visceral leishmaniasis. Drug Discov Today 18:1272-1281.
29. Maltezou H C. 2010. Drug resistance in visceral leishmaniasis. J Biomed Biotechnol 2010:617521.
30. Vanaerschot M, Dumetz F, Roy S, Ponte-Sucre A, Arevalo J, Dujardin J C. 2014. Treatment failure in leishmaniasis: drug-resistance or another (epi-) phenotype? Expert Rev Anti Infect Ther 12:937-946.
31. Sundar S, Chakravarty J. 2015. An update on pharmacotherapy for leishmaniasis. Expert Opin Pharmacother 16:237-252.
32. Cortes S, Albuquerque A, Cabral L I, Lopes L, Campino L, Cristiano M L. 2015. In Vitro Susceptibility of *Leishmania infantum* to Artemisinin Derivatives and Selected Trioxolanes. Antimicrob Agents Chemother 59:5032-5035.
33. Manda S, Khan S I, Jain S K, Mohammed S, Tekwani B L, Khan I A, Vishwakarma R A, Bharate S B. 2014. Synthesis, antileishmanial and antitrypanosomal activities of N-substituted tetrahydro-beta-carbolines. Bioorg Med Chem Lett 24:3247-3250.
34. Rahman A A, Samoylenko V, Jacob M R, Sahu R, Jain S K, Khan S I, Tekwani B L, Muhammad I. 2011. Antiparasitic and antimicrobial indolizidines from the leaves of Prosopis *glandulosa* var. *glandulosa*. Planta Med 77:1639-1643.
35. Jain S K, Sahu R, Walker L A, Tekwani B L. 2012. A parasite rescue and transformation assay for antileishmanial screening against intracellular *Leishmania donovani* amastigotes in THP1 human acute monocytic leukemia cell line. J Vis Exp doi:10.3791/4054.
36. Jain S, Jacob M, Walker L, Tekwani B. 2016. Screening North American plant extracts in vitro against *Trypanosoma brucei* for discovery of new antitrypanosomal drug leads. BMC Complementary and Alternative Medicine 16:1-6.
37. Hassan M, Watari H, AbuAlmaaty A, Ohba Y, Sakuragi N. 2014. Apoptosis and molecular targeting therapy in cancer. Biomed Res Int 2014:150845.
38. Maiese K, Chong Z Z, Shang Y C, Wang S. 2012. Targeting disease through novel pathways of apoptosis and autophagy. Expert Opin Ther Targets 16:1203-1214.
39. van Genderen H O, Kenis H, Hofstra L, Narula J, Reutelingsperger C P. 2008. Extracellular annexin A5: functions of phosphatidylserine-binding and two-dimensional crystallization. Biochim Biophys Acta 1783:953-963.
40. Wlodkowic D, Skommer J, Darzynkiewicz Z. 2012. Cytometry of apoptosis. Historical perspective and new advances. Exp Oncol 34:255-262.
41. Rieger A M, Nelson K L, Konowalchuk J D, Barreda D R. 2011. Modified annexin V/propidium iodide apoptosis assay for accurate assessment of cell death. J Vis Exp doi:10.3791/2597.

We claim:
1. Artemisinin dimers having the formula:

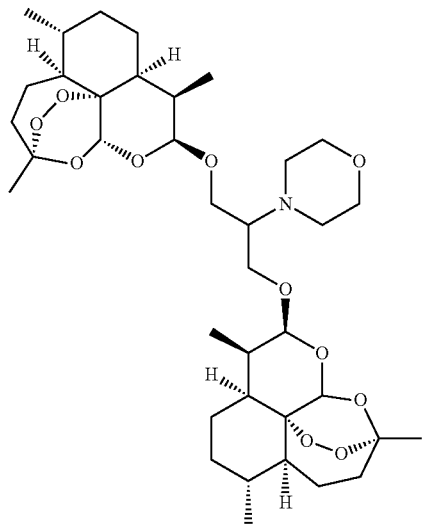

Dimer Morpholine

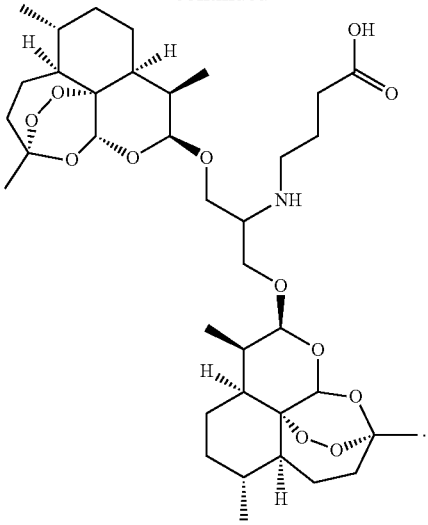

Dimer-GABA

2. A method of treating Leishmaniasis disease comprising administrating to a subject in need of such treatment an effective amount of at least one of the dimers according to claim 1.

3. A pharmaceutical composition comprising at least one dimer according to claim 1 and a suitable pharmaceutical carrier.

* * * * *